US006939900B2

(12) United States Patent
Ario et al.

(10) Patent No.: US 6,939,900 B2
(45) Date of Patent: Sep. 6, 2005

(54) DENTAL RESIN CEMENTS HAVING IMPROVED HANDLING PROPERTIES

(75) Inventors: Paula D. Ario, Woodbury, MN (US); Steven M. Aasen, Woodbury, MN (US); Brian N. Holmes, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/315,505

(22) Filed: Dec. 10, 2002

(65) Prior Publication Data

US 2003/0114554 A1 Jun. 19, 2003

Related U.S. Application Data

(63) Continuation of application No. 08/896,549, filed on Jul. 17, 1997, now Pat. No. 6,506,816.

(51) Int. Cl.[7] .............................................. A61K 6/087
(52) U.S. Cl. .................... 523/116; 433/215; 433/228.1; 523/115; 523/118; 524/533; 524/556; 524/559; 526/323.1
(58) Field of Search .................. 523/115–116, 118; 524/533, 556, 559; 526/323.1; 433/215, 228.1

(56) References Cited

U.S. PATENT DOCUMENTS

| | | |
|---|---|---|
| 3,018,262 A | 1/1962 | Schroeder |
| 3,117,099 A | 1/1964 | Proops et al. |
| 3,513,123 A | 5/1970 | Saffir |
| 3,655,605 A | 4/1972 | Smith |
| 3,814,717 A | 6/1974 | Wilson et al. |
| 4,143,018 A | 3/1979 | Crisp |
| 4,209,434 A | 6/1980 | Wilson et al. |
| 4,360,605 A | 11/1982 | Schmitt et al. |
| 4,376,835 A | 3/1983 | Schmitt et al. |
| 4,411,625 A | 10/1983 | Koblitz et al. |
| 4,503,169 A | 3/1985 | Randklev |
| 4,540,723 A | 9/1985 | Ying |
| 4,615,665 A | 10/1986 | Tateosian et al. |
| 4,648,844 A | 3/1987 | Omura et al. |
| 4,695,251 A | 9/1987 | Randklev |
| 4,746,686 A | 5/1988 | Waller |
| 4,792,577 A | 12/1988 | Chen et al. |
| 4,859,716 A | 8/1989 | Ibsen et al. |
| 5,034,433 A | 7/1991 | Cohen et al. |
| 5,154,762 A | 10/1992 | Mitra et al. |
| 5,204,398 A | 4/1993 | Cohen et al. |
| 5,332,429 A | 7/1994 | Mitra et al. |
| 5,403,188 A | 4/1995 | Oxman et al. |
| 5,530,038 A | 6/1996 | Yamamoto et al. |
| 5,709,548 A | 1/1998 | Oxman et al. |
| 5,753,781 A | 5/1998 | Oxman et al. |
| 5,965,632 A | 10/1999 | Orlowski et al. |
| 6,057,383 A | 5/2000 | Völkel et al. |
| 6,506,816 B1 * | 1/2003 | Ario et al. .................. 523/116 |

FOREIGN PATENT DOCUMENTS

| | | |
|---|---|---|
| EP | 0 438 629 A2 A3 | 7/1991 |
| EP | 0 533 434 A1 | 9/1992 |
| WO | WO 97/18792 | 5/1997 |

OTHER PUBLICATIONS

Handbook of Epoxy Resins By Lee and Neville, McGraw–Hill Book CO., New York (1967).
Aldrich Catalog; Milwaukee, Wisconsin; Title page, Publication Page, Table of Contents, and pp. 214 and 215 (5 pp. total) (2000–2001).
Sartomer Product Bulletin: SR–348, "Ethoxylated(3)Bisphenol A Dimethacrylate," Exton, PA; 1 page (Jan., 1999).
Sartomer Product Bulletin: CD–540, "Ethoxylated(4)Bisphenol A Dimethacrylate," Exton, PA; 1 page (Oct., 1998).
Sartomer Product Bulletin: CD–541, "Ethoxylated(6)Bisphenol A Dimethacrylate," Exton, PA; 1 page (Oct., 1998).
Sartomer Product Bulletin: SR–480, "Ethoxylated(10)Bisphenol A Dimethacrylate," Exton, PA; 1 page (Nov., 1998).
Sartomer Product Bulletin: SR–9036, "Ethoxylated(30)Bisphenol A Dimethacrylate," Exton, PA; 1 page (Jul., 1997).
Sartomer Product Bulletin: SR–602, "Ethoxylated(10)Bisphenol A Diacrylate," Exton, PA; 1 page (Dec., 1998).
Wilson et al., "Chapter 2: Compositions," *Glass–Ionomer Cement*; Quintessence Books; Chicago, London,Berlin, Sao Paulo, Tokyo, and Hong Kong; Title page, Table of Contents, and pp. 21–39 (1988).
Zwemer, Ed.; *Mosby's Dental Dictionary*; Mosby, Inc., St. Louis, Missouri; Title page, Publication page, and pp. 79–80 (4 pp. total) (1998).

* cited by examiner

*Primary Examiner*—Peter Szekely

(57) ABSTRACT

Dental resin cement materials having unique handling properties are provided that comprise a) filler, b) polymerizable resin, and c) a polymeric handling modifier that is dispersed in the polymerizable resin at 25° C. and that has a molecular weight of between about 500 and 100,000. Components a) b) and c) are present in an amount effective to achieve a Viscosity vs Shear Rate Curve that fits a power law model of $F(x)=Ax^B$. The correlation value of the material to this curve is greater than 0.85 for both the increasing and decreasing shear rate curves, and the value of B is less than about −0.01.

Resin cements are also provided that comprise acid functionality and water, but which do not comprise an acid reactive filler. Such cements may be self etching, thereby avoiding the need to carry out a separate acid etch step.

36 Claims, 1 Drawing Sheet

DENTAL RESIN CEMENTS HAVING IMPROVED HANDLING PROPERTIES

FIELD OF THE INVENTION

This invention relates to dental cements. More specifically, this invention relates to dental resin cements having surprising handling characteristics.

BACKGROUND OF THE INVENTION

Resin cements are utilized primarily for aesthetic bonding of aesthetic indirect appliances such as veneers, inlays, onlays, crowns and bridges. Resin cements generally provide excellent physical properties such as high compressive and tensile strength and low wear resistance, and are often used for bonding in difficult indirect bonding situations such as non-parallel or short crown preps.

Handling characteristics of currently commercially available resin luting cements for indirect appliances can cause difficulty in seating for indirect appliances due to resistance, clean-up difficulties due to low viscosity or shear dependence, fast or slow setting characteristics or stringiness.

SUMMARY OF THE INVENTION

Dental resin cement materials having unique handling properties are provided that comprise a) filler, b) polymerizable resin, and c) a polymeric handling modifier that is dispersed in the polymerizable resin at 25° C. and that has a molecular weight of between about 500 and 100,000. Components a) b) and c) are present in an amount effective to achieve a Viscosity vs Shear Rate Curve that fits a power law model of $F(x)=Ax^B$. The correlation value of the material to this curve is greater than 0.85 for both the increasing and decreasing shear rate curves, and the value of B is less than about −0.01.

Resin cements are also provided that comprise acid functionality and water, but which do not comprise an acid reactive filler. Such cements may be self etching, thereby avoiding the need to carry out a separate acid etch step.

DETAILED DESCRIPTION OF THE INVENTION

Figure 1:
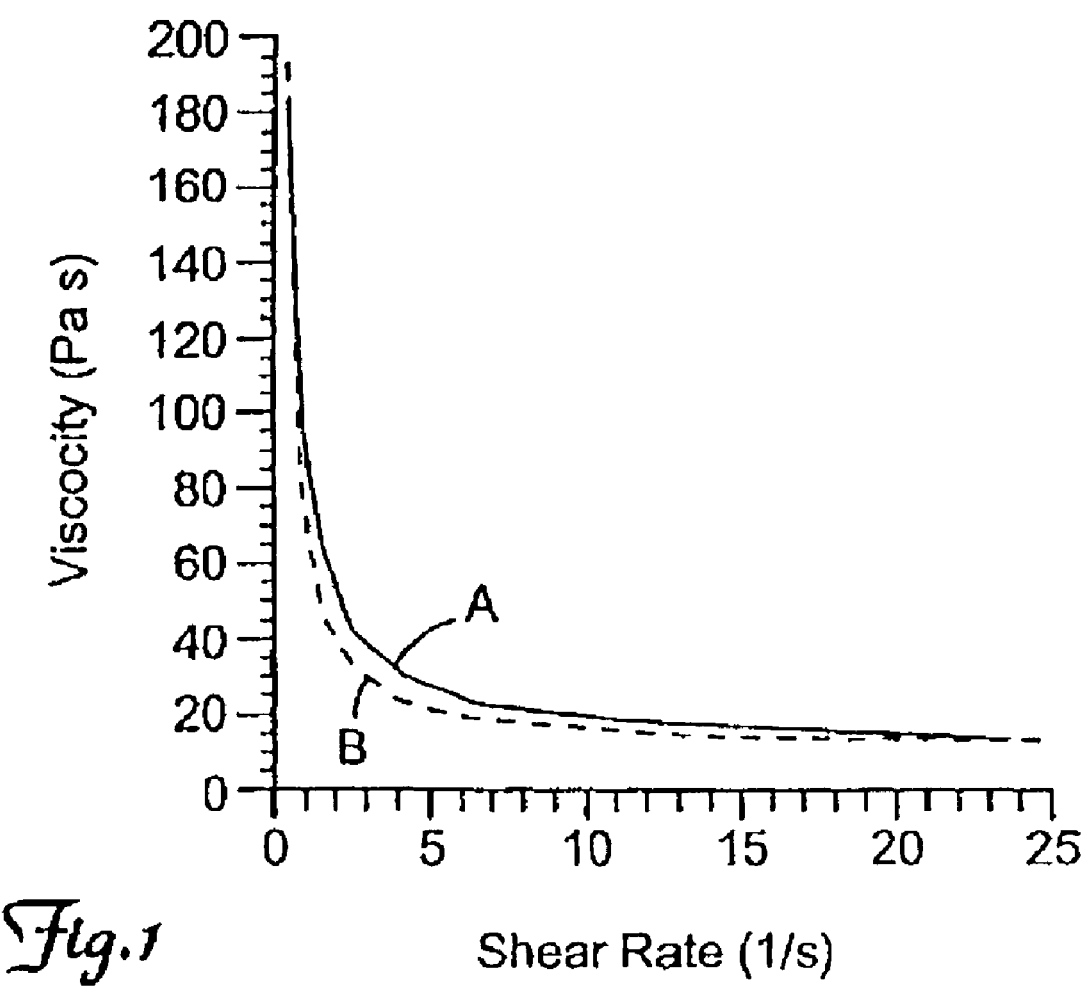
FIG. 1 shows a Viscosity vs Shear Rate Curve of a composition of the present invention.

Glass ionomer compositions possess excellent handling properties and can be easy to clean up after application in the oral environment, but are not as strong, have poor aesthetics, and have limited utility for certain bonding applications. Commercially available resin cements, in contrast, are strong, but are difficult to clean up during and after setting, and are not easily applied to the surfaces to be bonded. Clean up is the process of wiping, scraping or otherwise removing excess cement once a prefabricated prosthetic is placed in its tooth preparation.

The resin cements of the present invention have little to no resistance when placing a prefabricated prosthetic appliance. Cement clean-up is easier because there is little to no flow due to gravity once a prefabricated prosthetic device containing cement is seated. The cement is less stringy and messy, which makes placement onto or into a prefabricated prosthetic device easier. The cement is also brushable for ease of application, especially for use as a filled adhesive to bond restoratives. The cement also exhibits a moussy behavior on a mix pad before and after spatulation when other resin cements become runny after mixing. Cements containing handling modifier have a longer time period between work and set time than comparable resins not having a handling modifier. Longer set times may provide a more easily usable cement material because the practitioner has adequate time to ensure proper placement of the prosthetic device in the oral environment before cure of the cement, and the cement is less rigid and brittle at clean up.

For purposes of the present invention, "resin cements" are cements that are resin-based filled compositions that do not utilize water in its chemistry for curing. Thus, a resin cement does not contain a reactive filler, an acidic functionality and water at the same time, although a resin cement according to the present invention may contain any two of these three materials in the same composition. This is in contrast with glass ionomer cements, which utilize an ionomeric reaction to "set" the cement and require the presence of water to enable a reaction between acid functionalities and an acid-reactive glass.

For purposes of the present invention, the term "substantially free of added water" means that the composition does not contain water that is intentionally added as a non-complexed or coordinated entity. It is understood that many materials, such as metals or glasses, contain water that is taken up from the atmosphere or is present as a coordination complex in its normal state. Water taken up by hygroscopic materials or present as a hydrate is permissibly present in the compositions described herein. Any water that is present in the composition, regardless of source, should not be present in amounts such that the water will have a deleterious effect of the long term properties of the composition. For example, water should not be present in an amount that would facilitate reaction of any acid-reactive filler, if present, with any acidic component, if present, so that lumpiness or graininess of the material or degradation of initiators develops during commercially required storage time.

Components a) b) and c) are present in an amount effective to achieve a Viscosity vs Shear Rate Curve that fits a power law model of $F(x)=Ax^B$, and the value of B is less than about −0.01. In this model, F(x) is viscosity in Pascal seconds, x is shear rate in inverse seconds. Thus, a plot of the viscosity vs shear rate shows a decreasing viscosity as shear increases. It has surprisingly been found that the combination of filled dental material with handling modifier as defined herein provides this unusual physical behavior of these materials. Most surprisingly and beneficially, these materials exhibit this curve in both increasing and decreasing shear rate directions, thereby exhibiting reversible viscosity properties. The correlation value of the material to this curve is greater than 0.85 for both increasing and decreasing shear rate.

More preferably, the components are selected such that B is less than about −0.1, and more preferably B is between about −0.1 and −1.1.

Preferred dental cements are prepared by selection of materials such that A is greater than 10 and less than 3000, more preferably wherein A is greater than 15 and less than 1000, and most preferably wherein A is greater than 20 and less than 500.

Viscosity vs Shear Rate Curve

The viscosity of the dental materials described herein is measured at 25° C.±1° C. using a parallel plate controlled-stress or controlled strain rheometer. Because the measurements characterize a curve, good agreement has been found in the characterization of all materials regardless of the use of different equipment or slightly different plate diameter, use of sandpaper on the plate surface, or varying time between measurements.

In one set of experiments, the viscosity is measured using a Bohlin CS50 rheometer (Bohlin Instruments, NJ) with controlled stress at 25° C. The plate diameter was 20 mm, the separation between the plates was 1 mm, and the plates were sometimes lined with PSA-backed sandpaper (9 micrometer abrasive particle size) to prevent the material from slipping at the plate surface. The shear rate was ramped up from 0.5 to 20 sec$^{-1}$ and in reverse rate down to 0.5 from 20 sec$^{-1}$. This shear rate ramping took place every 40 or 60 seconds, with a 20 or 30 second delay time and 20 or 30 s integration time, for a total of 45 logarithmically-spaced shear rate steps per run (a run being defined as both increasing and decreasing shear direction).

In another set of experiments, the viscosity is measured using a Rheometric Dynamic Analyzer (Rheometrics, Inc., NJ) with controlled strain 26° C. The plate diameter was 25 mm, the separation between the plates was 1 mm, and the plates were sometimes lined with PSA-backed sandpaper (9 micrometer abrasive particle size) to prevent the material from slipping at the plate surface. The shear rate was ramped up from 0.4 to 25 sec$^{-1}$ and in reverse rate down to 0.4 from 25 sec$^{-1}$. This shear rate ramping took place every 40 seconds, with a 20 second delay time and a 20 second integration time, for a total of 10 logarithmically-spaced shear rate steps when ramped up or down.

Correlation of the datapoints to the curve is determined using standard curve-fitting analysis techniques, such as DeltaGraph version 2.0 graphing software.

Dental resin cements must be evaluated for exhibition of the above properties that will exhibit their observed properties under conditions of use. The skilled practitioner in the dental arts will recognize when a commercial material exhibits such properties through the ease of use of the product, i.e. the product will be of a moussy consistency, yet easily applied in a brushable format in a reversible manner such that once it is mixed or brushed it does not remain runny, but returns to its original moussy texture. Numerically demonstrating this characteristic may be difficult, because off-the-shelf products may contain polymerization initiators that will begin the cure process once the product is presented in its final use format. In the laboratory, the product development technician may easily evaluate proposed cement compositions by merely leaving out the polymerization initiator. Two part mixtures are preferably evaluated by testing each part separately to determine the characteristics of the viscosity/shear curve. If one side of a two-part mixture exhibits the power law model behavior, it is very likely that the combination of parts will exhibit this behavior as well. Quantitative testing can be carried out on the mixed product, however a qualitative evaluation of the behavior of the final product should be sufficient to confirm that the final product achieves the desired behavior described herein. If the product has a sufficiently long time before polymerization, tests may be carried out as long as permitted before significant viscosity changes occur to the cement through the polymerization process. For example, many commercial resin cements identify the working time of their cements, and the time available before significant viscosity changes will be noticed. Rheometer measurements may be taken on such materials until such viscosity increases affect the evaluation process, e.g. the first two minutes after mixing of a two part resin cement. Such a testing protocol may be required where the cement is provided as a powder/liquid two part material, and the viscosity behavior as taught herein is not evident until the parts are mixed.

Turning now to the specific materials as comprised in the present invention, the dental resin cement materials of the present invention comprise a polymeric handling modifier that is dispersed in the polymerizable resin at 25° C. and that has a molecular weight greater than about 500, and preferably between about 500 and 100,000.

For purposes of the present invention, the handling modifier will be considered to be dispersed in the resin if upon visual inspection by the unassisted eye one cannot discern more than one phase. Heating or other mixing techniques may be utilized to assist incorporation of the handling modifier into the resin matix, provided that upon return of the material to storage and use conditions, the handling modifier does not separate from the resin matrix. Many oligomers or polymers do not disperse adequately in the resin system, and therefore are not suitable as handling modifiers. An example of a polymer that is not suitable for methacrylate-based systems is paraffin wax, which does not disperse in traditionally preferred resin systems conventionally used in dental materials. Of course, the identification of suitable handling modifiers must be confirmed on a case-by-case basis utilizing the guidelines provided herein.

Preferably, the handling modifier is a polymer having a molecular weight between about 500 and 50,000, and most preferably between about 700–20,000. While no specific functionality is required on the compound to be used as the handling modifier, the presence of certain functionalities may assist in the dispersibility of the handling modifier by compatiblizing the modifier compound with the resin matrix. For example, it may be beneficial to provide polar functionalities or polymerizable functionalites in order to more easily disperse the handling modifier. The incorporation of polymerizable functionalities on the handling modifier that react using the same mechanism as the polymerizable resin additionally provides benefit in that the handling modifier would then react with the resin matix. Leeching or loss of modifier from the ultimately cured material may thereby be avoided. Further, the matrix may also benefit from added strength or lack of weak points due to unreacted modifier.

The handling modifier may alternatively or additionally be provided with acidic functionality. Such functionality may assist in dispersion of the handling modifier in the resin, and may also provide an etching action on the tooth structure, thereby providing a self-etching dental cement, or a cement that does not require a separate primer or adhesive to provide high adhesion to a tooth structure. The acidic group is preferably selected from oxyacids or thio-oxy acids of B, C, N, S, P. More preferably, the acidic component is a compound that is an acid of C or P. If desired, a precursor to the acid such as an acid anhydride, e.g., 4-Methacryloxyethyl Trimellitate Anhydride (4-META), or ester can be used in place of the acid itself, e.g., to generate the desired acid in situ. Suitable acids include, carboxylic acids, sulfonic acids, and phenols, with carboxylic acids, alkylsulfonic acids, arylsulfonic acids, phosphoric, phosphinic and phosphonic acids being preferred.

Preferably, the handling modifier is selected from the group consisting of methacrylate modified polycaprolactonediols, polycaprolactonediols (i.e., polycaprolactones), methacrylate modified polyethylene glycols, polyethylene glycol methyl ethers, methacrylate modified polytetramethylene oxides, polytetramethylene oxides, N-polyvinyl pyrrolidones (i.e., N-polyvinyl pyrrolidinones), polymeric ethoxylated Bisphenol A dimethacrylates (Bis-EMA), dicarboxy terminated polybutadienes, hydroxyl endcapped polybutadienes, and copolymers of Bisphenol A and epichlorohydrin.

Optionally, the handling modifier may be the same compound as the polymerizible resin as a whole. A particularly preferred cement comprises ethoxylated bisphenol A as the only polymerizable component or the major polymerizable component of the cement. The preferred ethoxylated bisphenol A is a reaction product of 6 moles of ethylene oxide and one mole of bisphenol-A, which in turn is reacted with 2 moles of methacrylic acid.

Generally, the handling modifier is present as less than 20% by weight of the dental material, or more preferably as less than 10% of the dental material.

Fillers may be selected from one or more of any material suitable for incorporation in compositions used for medical applications, such as fillers currently used in dental restorative compositions and the like. The filler is finely divided and preferably has a maximum particle diameter less than about 10 micrometers and an average particle diameter less than about 3.0 micrometers. More preferably, the filler has a maximum particle diameter less than about 2.0 micrometers and an average particle size of diameter less than about 0.6 micrometer. The filler can have a unimodal or polymodal (e.g., bimodal) particle size distribution. The filler can be an inorganic material. It can also be a crosslinked organic material that is insoluble in the polymerizable resin, and is optionally filled with inorganic filler. The filler should in any event be non-toxic and suitable for use in the mouth. The filler can be radiopaque, radiolucent or non-radiopaque.

Examples of suitable inorganic fillers are naturally-occurring or synthetic materials such as quartz, nitrides (e.g., silicon nitride), glasses derived from, for example Ce, Sb, Sn, Zr, Sr, Ba and Al, colloidal silica, feldspar, borosilicate glass, kaolin, talc, titania, and zinc glass; low Mobs hardness fillers such as those described in U.S. Pat. No. 4,695,251; and submicron silica particles (e.g., pyrogenic silicas such as the "Aerosil" Series "OX 50", "130", "150" and "200" silicas sold by Degussa and "Cab-O-Sil M5" silica sold by Cabot Corp.). Examples of suitable organic filler particles include filled or unfilled pulverized polycarbonates, polyepoxides, and the like. Preferred non-acid reactive filler particles are quartz, submicron silica, and non-vitreous microparticles of the type described in U.S. Pat. No. 4,503,169. Mixtures of these non-acid reactive fillers are also contemplated, as well as combination fillers made from organic and inorganic materials.

Preferably the surface of the filler particles is treated with a coupling agent in order to enhance the bond between the filler and the polymerizable resin. The use of suitable coupling agents include gamma-methacryloxypropyl-trimethoxysilane, gamma-mercaptopropyltriethoxysilane, gamma-aminopropyltrimethoxysilane, and the like.

Reactive fillers may be included compositions of the present invention, which may or may not have the property of releasing fluoride. Such fillers include those that are commonly used with ionomers to form ionomer cements. Examples of suitable reactive fillers include metal oxides such as zinc oxide and magnesium oxide, and ion-leachable glasses, e.g., as described in U.S. Pat. Nos. 3,655,605; 3,814,717; 4,143,018; 4,209,434; 4,360,605 and 4,376,835. Such reactive fillers may be incorporated to modify the handling characteristics or to affect the setting properties of the ultimate composition.

The reactive filler is preferably a finely divided reactive filler. The filler should be sufficiently finely-divided so that it can be conveniently mixed with the other ingredients and used in the mouth. Preferred average particle diameters for the filler are about 0.02 to about 15 micrometers, more preferably about 0.02 to 10 micrometers, as measured using, for example, a sedimentation analyzer.

Suitable acid-reactive fillers include metal oxides, metal salts and glasses. Preferred metal oxides include barium oxide, calcium oxide, magnesium oxide and zinc oxide. Preferred metal salts include salts of multivalent cations, for example aluminum acetate, aluminum chloride, calcium chloride, magnesium chloride, zinc chloride, aluminum nitrate, barium nitrate, calcium nitrate, magnesium nitrate, strontium nitrate and calcium fluoroborate. Preferred glasses include borate glasses, phosphate glasses and fluoroaluminosilicate glasses.

Most preferred of the acid reactive fillers are those that release fluoride. Fluoride releasing glasses, in addition to providing good handling and final composition properties as discussed above, provide the benefit of long-term release of fluoride in use, for example in the oral cavity. Fluoroaluminosilicate glasses are particularly preferred. Suitable acid reactive fillers are also available from a variety of commercial sources familiar to those skilled in the art. For example, suitable fillers can be obtained from a number of commercially available glass ionomer cements, such as "GC Fuji LC" and "Kerr XR" ionomer cement. Mixtures of fillers can be used if desired.

If desired, the acid reactive filler can be subjected to a surface treatment. Suitable surface treatments include acid washing, treatment with phosphates, treatment with chelating agents such as tartaric acid, treatment with a silane or silanol coupling agent. Particularly preferred acid reactive fillers are silanol treated fluoroaluminosilicate glass fillers, as described in U.S. Pat. No. 5,332,429 the disclosure of which is expressly incorporated by reference herein.

The polymerizable component of the present compositions are compounds, which may be monomers, oligomers, or polymers, containing a polymerizable group. These polymerizable groups may be selected from free radically polymerizable groups, cationically polymerizable groups, or mixtures thereof. Preferably, the polymerizable compound has a molecular weight of between about 100 to 5000, and more preferably, has a molecular weight between about 300 and 1000. Mixtures of both higher and lower molecular weight polymerizable materials are also contemplated as providing special benefits in handling properties and the physical properties of the ultimate cured material.

Preferred materials that provide the polymerizable component are the esters of acrylic or methacrylic acid. Examples of these compounds are methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate ("HEMA"), hydroxypropyl acrylate, hydroxypropyl methacrylate, tetrahydrofurfuryl acrylate, tetrahydrofurfuryl methacrylate, glycidyl acrylate, glycidyl methacrylate, the diglycidyl methacrylate of bis-phenol A ("Bis-GMA"), glycerol mono- and di-acrylate, glycerol mono- and di-methacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate [where the number of repeating ethylene oxide units vary from 2 to 30, especially triethylene glycol dimethacrylate ("TEGDMA")], neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxethyl hexamethylene dicarbamate, di-2-methacryloyloxyethyl trimethylhexamethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethyl-hexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl-4-cyclohexyl carbamate, 2,2'-bis(4-methacryloxyphenyl)propane, 2,2'bis(4-acryloxyphenyl) propane, 2,2'-bis[4(2-hydroxy-3-methacryloxy-phenyl)] propane, 2,2'-bis[4(2-hydroxy-3-acryloxy-phenyl) propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, 2,2'-bis[3(4-phenoxy)-2-hydroxypropane-1-acrylate]propane, and the like.

Other preferred polymerizable components can be substituted acryl amides and methacrylamides. Examples are acrylamide, methylene bis-acrylamide, methylene bis-methacrylamide, diacetone/acrylamide diacetone methacylamide, N-alkyl acrylamides and N-alkyl methacrylamides where alkyl is a lower hydrocarbyl unit. Other suitable examples of polymerizable components are isopropenyl oxazoline, vinyl azalactone, vinyl pyrrolidone, styrene, divinylbenzene, urethane acrylates or methacrylates, epoxy acrylates or methacrylates and polyol acrylates or methacrylates.

Alternatively, the polymerizable component may be a cationically cured material, such as epoxy materials, oxetanes, oxolanes, cyclic acetals, lactams, lactones, and vinyl ethers or spirocyclic compounds containing O atoms in the rings.

The cationically polymerizable epoxy resins useful in the compositions of the invention comprise organic compounds having an oxirane ring, i.e.,

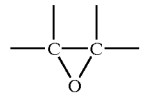

polymerizable by ring opening. Such materials, broadly called epoxides, include monomeric epoxy compounds and epoxides of the polymeric type and can be aliphatic, cycloaliphatic, aromatic or heterocyclic. These materials generally have, on the average, at least 1 polymerizable epoxy group per molecule, and preferably at least about 1.5 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures containing one, two, or more epoxy groups per molecule. The "average" number of epoxy groups per molecule is determined by dividing the total number of epoxy groups in epoxy-containing material by the total number of epoxy molecules present.

These epoxy-containing materials may vary from low molecular weight monomeric materials to high molecular weight polymers and may vary greatly in the nature of their backbone and substituent groups. For example, the backbone may be of any type and substituent groups thereon can be any group that does not substantially interfere with cationic cure at room temperature. Illustrative of permissible substituent groups include halogens, ester groups, ethers, sulfonate groups, siloxane groups, nitro groups, phosphate groups, and the like. The molecular weight of the epoxy-containing materials may vary from about 58 to about 100,000 or more.

Useful epoxy-containing materials include those which contain cyclohexene oxide groups such as the epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexylmethyl) adipate. For a more detailed list of useful epoxides of this nature, reference is made to the U.S. Pat. No. 3,117,099, incorporated herein by reference.

Further epoxy-containing materials which are particularly useful in the practice of this invention include glycidyl ether monomers of the formula

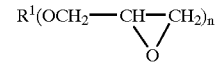

where $R^1$ is alkyl or aryl and n is an integer of 1 to 6. Examples are glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)-propane). Further examples of epoxides of this type which can be used in the practice of this invention are described in U.S. Pat. No. 3,018,262, incorporated herein by reference, and in "Handbook of Epoxy Resins" by Lee and Neville, McGraw-Hill Book Co., New York (1967).

There are a host of commercially available epoxy resins which can be used in this invention. In particular, epoxides which are readily available include octadecylene oxide, epichlorohydrin, styrene oxide, vinyl cyclohexene oxide, glycidol, glycidylmethacrylate, diglycidyl ether of Bisphenol A (e.g., those available under the trade designations "Epon 828", "Epon 825", "Epon 1004" and "Epon 1010" from Shell Chemical Co., "DER-331", "DER-332", and "DER-334", from Dow Chemical Co.), vinylcyclohexene dioxide (e.g., "ERL-4206" from Union Carbide Corp.), 3,4-epoxycyclohexylmethyl-3,4-epoxycyclohexene carboxylate (e.g., "ERL-4221" or "UVR 6110" or " UVR 6105" from Union Carbide Corp.), 3,4-epoxy-6-methylcyclohexylmethyl-3,4-epoxy-6-methyl-cyclohexene carboxylate (e.g., "ERL-4201" from Union Carbide Corp.), bis (3,4-epoxy-6-methylcyclohexylmethyl) adipate (e.g., "ERL-4289" from Union Carbide Corp.), bis(2,3-epoxycyclopentyl) ether (e.g., "ERL-0400" from Union Carbide Corp.), aliphatic epoxy modified with polypropylene glycol (e.g., "ERL-4050" and "ERL-4052" from Union Carbide Corp.), dipentene dioxide (e.g., "ERL-4269" from Union Carbide Corp.), epoxidized polybutadiene (e.g., "Oxiron 2001" from FMC Corp.), silicone resin containing epoxy functionality, flame retardant epoxy resins (e.g., "DER-580", a brominated bisphenol type epoxy resin available from Dow Chemical Co.), 1,4-butanediol diglycidyl ether of phenolformaldehyde novolak (e.g., "DEN-431" and "DEN-438" from Dow Chemical Co.), and resorcinol diglycidyl ether (e.g., "Kopoxite" from Koppers Company, Inc.). bis(3,4-epoxycyclohexyl)adipate (e.g., "ERL-4299" or "UVR-6128", from Union Carbide Corp.), 2-(3,4-epoxycyclohexyl-5,5-spiro-3,4-epoxy) cyclohexane-metadioxane (e.g., "ERL-4234" from Union Carbide Corp.), vinylcyclohexene monoxide (from Union Carbide Corp.), 1,2-epoxyhexadecane (e.g., "UVR-6216" from Union Carbide Corp.), alkyl glycidyl ethers such as alkyl $C_8$–$C_{10}$ glycidyl ether (e.g., "HELOXY Modifier 7" from Shell Chemical Co.), alkyl $C_{12}$–$C_{14}$ glycidyl ether (e.g., "HELOXY Modifier 8" from Shell Chemical Co.), butyl glycidyl ether (e.g., "HELOXY Modifier 61" from Shell Chemical Co.), cresyl glycidyl ether (e.g., "HELOXY Modifier 62" from Shell Chemical Co.), p-tert butylphenyl glycidyl ether (e.g., "HELOXY Modifier 65" from Shell Chemical Co.), polyfunctional glycidyl ethers such as diglycidyl ether of 1,4-butanediol (e.g., "HELOXY Modifier 67" from Shell Chemical Co.), diglycidyl ether of neopentyl glycol (e.g., "HELOXY Modifier 68" from Shell Chemical Co.), diglycidyl ether of cyclohexanedimethanol (e.g., "HELOXY Modifier 107" from Shell Chemical Co.), trimethylol ethane triglycidyl ether (e.g., "HELOXY Modifier 44" from Shell Chemical Co.), trimethylol propane triglycidyl ether (e.g., "HELOXY Modifier 48" from Shell Chemical Co.), polyglycidyl ether of an aliphatic polyol (e.g.,. "HELOXY Modifier 84" from Shell Chemical Co.), polyglycol diepoxide (e.g., "HELOXY Modifier 32" from Shell Chemical Co.), bisphenol F epoxides (e.g., "EPN-1138" or "GY-281" from Ciba-Geigy Corp.), 9,9-bis[4-(2,3-epoxypropoxy)-phenyl]fluorenone (e.g., "Epon 1079" from Shell Chemical Co.).

Still other epoxy resins contain copolymers of acrylic acid esters or glycidol such as glycidylacrylate and glycidylmethacrylate with one or more copolymerizable vinyl compounds. Examples of such copolymers are 1:1 styrene-glycidylmethacrylate, 1:1 methylmethacrylate-glycidylacrylate and a 62.5:24:13.5 methylmethacrylate-ethyl acrylate-glycidylmethacrylate.

Other useful epoxy resins are well known and contain such epoxides as epichlorohydrins, e.g., epichlorohydrin; alkylene oxides, e.g., propylene oxide, styrene oxide; alkenyl oxides, e.g., butadiene oxide; glycidyl esters, e.g., ethyl glycidate.

The polymers of the epoxy resin may optionally contain other functionalities that do not substantially interfere with cationic cure at room temperature.

Blends of various epoxy-containing materials are particularly contemplated in this invention. Examples of such blends include two or more molecular weight distributions of epoxy-containing compounds, such as low molecular weight (below 200), intermediate molecular weight (about 200 to 10,000) and higher molecular weight (above about 10,000). Alternatively or additionally, the epoxy resin may contain a blend of epoxy-containing materials having different chemical nature, such as aliphatic and aromatic, or functionality, such as polar and non-polar. Other cationically polymerizable polymers may additionally be incorporated. Particularly preferred epoxy containing compositions also contain materials having hydroxyl functionality.

Mixtures of polymerizable materials, including hybrid systems containing both free-radically polymerized components and cationically polymerized components, are also contemplated.

Compositions of the invention contain one or more suitable polymerization initiators, so that the composition may be polymerized in use. The initiator is selected such that it is capable of initiating the polymerization of the polymerizable material. That is, if the polymerizable material is a free radical polymerizable material, the initiator is a free-radical polymerization initiator. Likewise, if the polymerizable material is a cationically polymerizable material, the initiator is a cationic polymerization initiator. Generally, one-part dental resin cement compositions are preferred, so that compositions using a photoinitiator system are preferred. However, in many applications of dental resin cements it is difficult if not impossible to expose the cement to the light of a curing lamp, so initiator systems that are capable of curing without light are very desirable as well.

Compositions of the invention that are free-radically polymerized preferably contain one or more suitable photopolymerization initiators that act as a source of free radicals when activated. Such initiators can be used alone or in combination with one or more accelerators and/or sensitizers.

The photoinitiator should be capable of promoting free radical crosslinking of the ethylenically unsaturated moiety on exposure to light of a suitable wavelength and intensity. It also preferably is sufficiently shelf stable and free of undesirable coloration to permit its storage and use under typical dental conditions. Visible light photoinitiators are preferred. The photoinitiator frequently can be used alone, but typically it is used in combination with a suitable donor compound or a suitable accelerator (for example, amines, peroxides, phosphorus compounds, ketones and alpha-diketoine compounds).

Preferred visible light-induced initiators include camphorquinone (which typically is combined with a suitable hydrogen donor such as an amine), diaryliodonium simple or metal complex salts, chromophore-substituted halomethyl-s-triazines and halomethyl oxadiazoles. Particularly preferred visible light-induced photoinitiators include combinations of an alpha-diketone, e.g., camphorquinone, and a diaryliodonium salt, e.g., diphenyliodonium chloride, bromide, iodide or hexafluorophosphate, with or without additional hydrogen donors (such as sodium benzene sulfinate, amines and amine alcohols).

Preferred ultraviolet light-induced polymerization initiators include ketones such as benzyl and benzoin, and acyloins and acyloin ethers. Preferred commercially available ultraviolet light-induced polymerization initiators include 2,2-dimethoxy-2-phenylacetophenone ("IRGACURE 651") and benzoin methyl ether (2-methoxy-2-phenylacetophenone), both from Ciba-Geigy Corp.

The photoinitiator should be present in an amount sufficient to provide the desired rate of photopolymerization. This amount will be dependent in part on the light source, the thickness of the layer to be exposed to radiant energy, and the extinction coefficient of the photoinitiator. Typically, the photoinitiator components will be present at a total weight of about 0.01 to about 5%, more preferably from about 0.1 to about 5%, based on the total weight of the composition.

The compositions of the present invention may alternatively incorporate a mode of initiation of the polymerization reaction to initiate a crosslinking reaction without the need to expose the system to visible light. A preferred alternative mode for initiation of the polymerization reaction is the incorporation of an oxidizing agent and a reducing agent as a redox catalyst system to enable the dental composition to cure via a redox reaction. Various redox systems is described in U.S. Pat. No. 5,154,762, the disclosure of which is expressly incorporated herein by reference.

The oxidizing agent should react with or otherwise cooperate with the reducing agent to produce free radicals capable of initiating polymerization of the ethylenically unsaturated moiety. The oxidizing agent and the reducing agent preferably are sufficiently shelf stable and free of undesirable coloration to permit their storage and use under typical dental conditions. The oxidizing agent and the reducing agent should also preferably be sufficiently soluble and present in an amount sufficient to permit an adequate free radical reaction rate. This can be evaluated by combining the ethylenically unsaturated moiety, the oxidizing agent and the reducing agent and observing whether or not a hardened mass is obtained.

Suitable oxidizing agents include persulfates such as sodium, potassium, ammonium and alkyl ammonium persulfates, benzoyl peroxide, hydroperoxides such as cumene hydroperoxide, tert-butyl hydroperoxide, tert-amyl hydroperoxide and 2,5-dihydroperoxy-2,5-dimethylhexane, salts of cobalt (III) and iron (III), hydroxylamine, perboric acid and its salts, salts of a permanganate anion, and combinations thereof Hydrogen peroxide can also be used, although it may, in some instances, interfere with the photoinitiator, if one is present. The oxidizing agent may optionally be provided in an encapsulated form as described in U.S. Pat. No. 5,154,762.

Preferred reducing agents include amines (and preferably aromatic amines), ascorbic acid, metal complexed ascorbic acid, cobalt (II) chloride, ferrous chloride, ferrous sulfate, hydrazine, hydroxylamine, oxalic acid, thiourea and salts of a dithionite, thiosulfate, benzene sulfinate, or sulfite anion.

When redox initiator systems are used to photoinitiator systems, because care must be taken to keep the reducing agent from reacting with the oxidizing agent before polymerization is desired. Generally, the use of a redox system necessitates providing the material in a two-part format.

For compositions that are polymerized by a cationic mechanism, suitable initiators include salts that are capable of generating cations such as the diaryliodonium, triarylsulfonium and aryldiazonium salts. Use of electronic donors or peroxides in such systems are also useful for enhancing rate of cure and depth of cure. Simultaneous photoinitiation of cationic and free radical groups may be afforded by, for example, onium salts or organometallic compounds in combination with or without oxidizing agents. Organometallic compounds can be selected from compounds that undergo sigma bond cleavage upon photolysis. The sigma bond is usually a metal—metal bond. Examples of suitable organometallic compounds include $[\text{Co Fe(Co)}_2]_2$, $\text{Mn(CO)}_{10}$, and $\text{Mn}_2(\text{CO})_{10}$, in combination with iodonium salts and peroxides.

If desired, the compositions of the invention can contain adjuvants such as cosolvents, pigments, inhibitors, accelerators, surfactants, colorants, medicaments and other ingredients that will be apparent to those skilled in the art. Optionally, the compositions may contain stabilizers.

The fluoride-releasing materials may also be provided, which may be naturally occurring or synthetic fluoride minerals, fluoride glass such as fluoroaluminosilicate glass, simple and complex inorganic fluoride salts, simple and complex organic fluoride salts or combinations thereof. Optionally these fluoride sources can be treated with surface treatment agents.

Examples of the fluoride-releasing material are fluoroaluminosilicate glasses described in U.S. Pat. No 4,3814,717, which may be optionally treated as described in U.S. Pat. No. 5,332,429, the disclosures of which are both incorporated by reference herein.

The dental materials of the present invention may be manufactured by mixing the filler, polymerizable resin, and handling modifier together. It may be preferable to mix the polymerizable resin and the handling modifier together first, followed by addition of the filler. It may be desirable to provide heat or to utilize other mixing techniques to ensure complete mixing of the modifier in the polymerizable resin, provided that the handling modifier must eventually be dispersed in the polymerizable resin at 25° C. If the initial mixture is found to have insufficient viscosity, more handling modifier and/or filler is added to provide the correct initial viscosity. Commercially available cements may be modified in accordance with the present invention by adding handling modifier as defined herein and reducing the amount of filler if needed, thereby imparting the desired reverse rate viscosity curve.

The resin cements of the present invention may be used to place a number of materials, such as dental restoratives or prefabricated prosthetic devices. Examples of prefabricated prosthetic devices include crowns, bridges, veneers, inlays, onlays, posts, pins, and the like. Examples of restoratives include dental composites and amalgams. A hard oral surface is any surface found in the oral environment suitable for bonding to, including enamel and dentin surfaces of the tooth, and any preexisting appliances or other structure in the oral environment, such as crowns, bridges, previously placed restoratives, or the like. A prepared surface is one where the surface has been cleaned and, if necessary, drilled, abraded or otherwise prepared for subsequent adhesion thereto. In the context of the present invention, the step of surface preparation does not include acid etching of the surface.

A method of placing a prefabricated prosthetic device, comprises a) preparing an oral surface, b) applying a dental resin cement of the present invention to a device, c) seating the device on the prepared oral surface, and d) cleaning off the excess resin cement from the margin between said oral surface and said device.

A method of adhering a direct restorative material comprises a) preparing an oral surface, b) applying a dental resin cement of the present invention to said prepared oral surface, and c) placing a direct restorative material on said cement applied to the prepared oral surface.

Where a particularly strong bond to oral surface is desired, a method of adhering to a hard oral surface comprises, a) etching said oral surface, b) applying an adhesive composition comprising polymerizable monomer and polymerization initiator to said etched oral surface, c) causing said adhesive composition to polymerize on said surface, d) applying a resin cement of the present invention to said adhesive treated surface, and e) causing said resin cement to polymerize.

Similarly, prefabricated prosthetic devices may be strongly adhered to a hard oral surface by a) etching said oral surface, b) applying an adhesive composition comprising polymerizable monomer and polymerization initiator to said etched oral surface, c) causing said adhesive composition to polymerize on said surface, d) applying a resin cement of the present invention to said prefabricated prosthetic device, e) seating the device on the prepared oral surface, and f) cleaning off the excess resin cement from the margin between said oral surface and said device.

DETAILED DESCRIPTION OF THE DRAWING

FIG. 1 shows a Viscosity vs Shear Rate Curve of a composition of the present invention. Curve A shows the viscosity at increasing shear rate, and Curve B shows the viscosity at decreasing shear rate. As can be observed, the curve follows a power law model of $F(x)=Ax^B$.

EXAMPLES

The following examples are given to illustrate, but not limit, the scope of this invention. Unless otherwise indicated, all parts and percentages are by weight, and all molecular weights are weight average molecular weight.

Preparatory Example 1

Treated OX-50

A-174 (3.7 g) was added with stirring to 50 g of deionized water acidified to pH 3–3.3 by dropwise addition of trifluoroacetic acid. The resultant mixture was stirred at about 25° C. for 1 hour at which time 95 g of fumed silica having a surface area of 40–50 m$^2$/g (OX-50) were added to the mixture with continued stirring for 4 hours. The slurry was poured into a plastic-lined tray and dried at 35° C. for 36 hours. The silanol treated dried powder was sieved through a 74 micrometer mesh screen.

Preparatory Example 2

Silanol Treated Reactive Glass 2.43 parts of A174 silane is added to 0.33 parts of glacial acetic acid and 36.47 parts of deionized water, and stirred vigorously to hydrolyze for 1 hour. After 1 hour, 60.78 parts of the MoSci glass M35M-2000 that has been ethanol-treated MoSci glass milled with ½" ceramic media for 3 hours and 42 minutes and screened through a 400 mu sieve and ground in a PK blender for 15 minutes is added to the solution and allowed to slurry for 30 minutes. The treated glass is dried, crushed and screened through a 74 micrometer screen.

Preparatory Example 3

Reactive Powder 96.6 parts of SP940-S Glass Frit Specialty Glass, OLDSMAR, Fla. is milled with 0.483 methanol (AR Grade), 0.966 sodium phosphate, and 1.951 parts of iodonium chloride. The resulting powder is screened through a 74 micrometer screen.

Preparatory Example 4

Silanol Treated Zirconia/Silica Filler

1% of triflouroacetic acid is added as required to 32.47 parts of deionized water and stirred for 5 minutes to attain a target pH range of 3.20–3.50. Add 2.60 parts of A-174 silane, and mixed. Add 64.94 parts of zirconia silica (average particle size 1.2–1.60 micrometers) slowly over 15 minutes, and mixed for a total of 90 minutes. The slurry is dried, and the resulting cakes are crushed, dried, and screened through a 74 micron mesh screen.

Preparatory Example 5

Blended Fillers 95.2 parts of zirconia silica of average particle size 1.2–1.6 micrometers is blended with 4.8 parts OX50 fumed silica with a surface area of 40–50 m$^2$/g. This blend is silanol treated.

Preparatory Example 6

Silanol Treated Zirconia Silica Filler

One hundred parts zirconia silica filler of average particle size 0.6–0.9 micrometers is mixed with deionized water at a solution temperature of between 20–30 C., and the pH is adjusted to 3–3.3 with Trifluoroacetic acid (TFAA) (0.278 parts). A-174 silane (11.14 parts) is added to the slurry and the blend is mixed over 2 hours. At the end of 2 hours, a calcium hydroxide (0.299 parts) water solution is added to the tank. The filler is dried, crushed and screened through a 74 or 100 micron screen.

Example 1

The cement formulation used consists of 3.75% 2 equivalents of isocyanatoethyl methacrylate reacted with polycaprolactone molecular weight 1250 g/mole (tone 0230, Union Carbide), 14.6% triethyleneglycol dimethacrylate, 14.6% Bis-GMA and 68% of a blend of 10% the filler of Preparatory Example 1 and 90% of the filler of Preparatory Example 4.

Example 2

The cement formulation used consists of 17% Terathane (polytetrahydrofuran) 2900, 18% 2-hydroxyethyl methacrylate, 14.6% Bis-GMA and 65% of a blend of 10% of the filler of Preparatory Example 1 and 90% of the filler of Preparatory Example 4.

Example 3

The cement formulation used consists of 32% 6 mole ethoxylated Bisphenol-A dimethacrylate and 68% of the filler of Preparatory Example 4.

Example 4

The cement formulation used consists of 3.75% polycaprolactonediol 1250 g/mole (TONE0230, Union Carbide), 14.6% triethyleneglycol dimethacrylate, 14.6% Bis-GMA and 68% of a blend of 10% of the filler of Preparatory Example 1 and 90% of the filler of Preparatory Example 4.

Example 5

The cement formulation used consists of 32% 6 mole ethoxylated Bisphenol-A dimethacrylate and 68% of a blend of 10% of the filler of Preparatory Example 1 and 90% of the filler of Preparatory Example 4.

Example 6

The cement formulation used consists of 3.75% 2 equivalents of isocyanatoethyl methacrylate reacted with polycaprolactonediol molecular weight 1250 g/mole (TONE0230, Union Carbide), 14.6% triethyleneglycol dimethacrylate, 14.6% Bis-GMA and 73% of a blend of 10% of the filler of Preparatory Example 1 and 90% of the filler of Preparatory Example 4.

Example 7

The cement formulation consists of 27% 6 mole ethoxylated Bisphenol-A dimethacrylate and 73% of a blend of 10% of the filler of Preparatory Example 1 and 90% of the filler of Preparatory Example 4.

Example 8

The cement formulation consists of 32% 6 mole ethoxylated Bisphenol-A dimethacrylate and 68% of the filler of Preparatory Example 3.

Example 9

The cement formulation consists of 37% 6 mole ethoxylated Bisphenol-A dimethacrylate and 63% of a blend of 10% of the filler of Preparatory Example 1 and 90% of the filler of Preparatory Example 4.

Example 10

The cement formulation consists of 7% of polyethylene glycol 1000 g/mole (PEG) encapped with 1 equivalent of 2-hydroxyethyl methacrylate(HEMA) and 1 equivalent of toluene diisocyanate(TDI), 12.5% triethyleneglycol dimethacrylate, 12.5% Bis-GMA and 68% of a blend of 10% of the filler of Preparatory Example 1 and 90% of the filler of Preparatory Example 4.

Example 11

The cement formulation used consists of 45% polycaprolactonediol (TONE0230), 13.75% triethyleneglycol dimethacrylate, 13.75% Bis-GMA and 68% of a blend of 10% of the filler of Preparatory Example 1 and 90% of the filler of Preparatory Example 4.

Example 12

The cement formulation used consists of 4% polycaprolactonediol 3000 g/mole (TONE0260 Union Carbide), 14% triethyleneglycol dimethacrylate, 14% Bis-GMA and 68% of a blend of 10% of the filler of Preparatory Example 1 and 90% of the filler of Preparatory Example 4.

Example 13

The cement formulation used consists of 4% of a copolymer of bisphenol-A and epichlorohydrin 1075 g/mole, 14.6% triethyleneglycol dimethacrylate, 14.6% Bis-GMA and 68% of a blend of 10% of the filler of Preparatory Example 1 and 90% of the filler of Preparatory Example 4.

Example 14

The cement formulation used consists of 4.5% 2 equivalents of isocyanatoethyl methacrylate reacted with polycaprolactonediol (TONE0230) g/mole, 11.25% triethyleneglycol dimethacrylate, 11.25% Bis-GMA and 73% of the filler of Preparatory Example 4.

Example 15

The cement formulation used consists of 1.5% N-polyvinylpyrrolidinone k2932 (International Specialty Products, Wayne, N.J.), 17.0% Bis-GMA, 15.25% 2-hydroxyethyl methacrylate and 68% of a blend of 10% of the filler of Preparatory Example 1 and 90% of the filler of Preparatory Example 4.

Example 16

The cement formulation used consists of 4.3% polycaprolactonediol molecular weight 3000 g/mole (TONE0260), 13.85% triethyleneglycol dimethacrylate, 13.85% Bis-GMA and 68% of a blend of 10% of the filler of Preparatory Example 1 and 90% of the filler of Preparatory Example 4.

Example 17

The cement formulation used consists of 29% of 6 mole Bis-EMA and 71% of the filler of Preparatory Example 2.

Example 18

The cement formulation used consists of 4% polyethyleneglycol methyl ether 2000 g/mole, 14% Bis-GMA, 14% 2-hydroxyethyl methacrylate and 68% of a blend of 10% of the filler of Preparatory Example 1 and 90% of the filler of Preparatory Example 4.

Example 19

The cement formulation used consists of 4% polycaprolactonediol molecular (TONE 0240), 14% triethyleneglycol dimethacrylate, 14% Bis-GMA and 68% of a blend of 10% of the filler of Preparatory Example 1 and 90% of the filler of Preparatory Example 4.

Example 20

The cement formulation used consists of 30% 10 mole ethoxylated Bisphenol-A dimethacrylate, 1.5% triethyleneglycol dimethacrylate, and 68% of a blend of 10% of the filler of Preparatory Example 1 and 90% of the filler of Preparatory Example 4.

Example 21

The cement formulation used consists of 2% polycaprolactone molecular weight 3000 g/mole (TONE0260), 13.85% TRIETHYLENEGLYCOL DIMETHACRYLATE, 13.85% Bis-GMA and 68% of a blend of 10% of the filler of Preparatory Example 1 and 90% of the filler of Preparatory Example 4.

Example 22

The cement formulation used consists of 18% 2-hydroxy ethyl methacrylate, 43% of the filler of Preparatory Examples, 22% of the filler of Preparatory Example 6, and 17% of a polymer of 2 equivalents of 2-phosphonooxy ethyl methacrylate and 1 equivalent of terethane (polytetrahydrofuran) 2900.

Example 23

The cement formulation consists of 16% triethyleneglycol dimethacrylate, 16% 6 mole Bis-EMA and 68% of the filler of Preparatory Example 6.

Example 24

The cement formulation consists of 32% 6-mole ethoxylated Bisphenol-A dimethacrylate (6 mole Bis-EMA), 25% of the filler of Preparatory Example 6 and 43% of the filler of Preparatory Example 5.

Example 25

The cement formulation used consists of 4% hydroxyl endcapped polybutadiene 2800 g/mole, 14.6% triethyleneglycol dimethacrylate, 14.6% Bis-GMA and 68% of a blend of 10% of the filler of Preparatory Example 1 and 90% of the filler of Preparatory Example 4.

Example 26

The cement formulation used consists of 4% 2 equivalents of isocyanatoethyl methacrylate reacted with polycaprolactone molecular weight 1250 g/mole, 14.6% triethyleneglycol dimethacrylate, 14.6% Bis-GMA, 25% of the filler of Preparatory Example 6 and 45% of the filler of Preparatory Example 5.

| Example | Rheology A Up | Rheology A Down | Rheology B up | Rheology B Down | Rheology measurements s-paper | sec | rhmtr | Correlation Up | Down |
|---|---|---|---|---|---|---|---|---|---|
| 1 | 111.9 | | −0.6979 | | nsp | 60 | B | 0.99074 | |
| 2 | 334.3 | | −0.7781 | | sp | 40 | B | 0.99949 | |
| 3 | 57.09 | | −0.4713 | | sp | 40 | B | 0.99205 | |
| 4 | 67.98 | | −0.5282 | | sp | 40 | B | 0.99085 | |
| 5 | 153.3 | | −0.5673 | | sp | 40 | B | 0.9969 | |
| 6 | 200.4 | | −0.8596 | | sp | 40 | B | 0.98058 | |
| 7 | 257.3 | | −0.7298 | | sp | 40 | B | 0.98131 | |
| 8 | 50.93 | | −0.2974 | | sp | 40 | B | 0.96129 | |
| 9 | 65.01 | | −0.5298 | | sp | 40 | B | 0.99570 | |
| 10 | 130.5 | 101.3 | −0.4939 | −0.4722 | sp | 40 | R | 0.9938 | 0.9686 |
| 11 | 86.61 | 65.93 | −0.4457 | −0.4129 | sp | 40 | R | 0.9879 | 0.9320 |
| 12 | 128.0 | 85.86 | −0.4533 | −0.4544 | sp | 40 | R | 0.9910 | 0.9695 |
| 13 | 80.47 | | −0.4823 | | sp | 60 | B | 0.9850 | |
| 14 | 220.5 | | −0.6785 | | nsp | 60 | B | 0.97680 | |
| 15 | 259.5 | | −0.8351 | | nsp | 60 | B | 0.97116 | |
| 16 | 232.0 | | −0.7004 | | sp | 60 | B | 0.95968 | |
| 17 | 305.9 | | −0.5936 | | sp | 60 | B | 0.85008 | |
| 18 | 78.35 | 119.55 | −0.5331 | −0.39712 | sp | 40 | R | 0.93103 | 0.93711 |
| 19 | 207.3 | 84.71 | −0.5574 | −0.5034 | sp | 40 | R | 0.9869 | 0.9735 |
| 20 | 92.76 | | −0.5238 | | sp | 40 | R | 0.9880 | |
| 21 | 76.60 | 47.84 | −0.3578 | −0.3115 | sp | 40 | R | 0.9932 | 0.8910 |
| 22 | 480.13 | 391.30 | −0.78891 | −0.77335 | sp | 40 | R | 0.9955 | 0.9985 |
| 23 | 137.5 | | −0.7672 | | sp | 40 | B | 0.96509 | |
| 24 | 156.1 | | −0.4758 | | sp | 40 | B | 0.98859 | |
| 25 | 73.70 | | 0.8990 | | nsp | 60 | B | 0.97092 | |
| 26 | 346.7 | 126.2 | −0.5546 | −0.4660 | sp | 40 | R | 0.9747 | 0.9516 |
| | | | | | sp | 40 | | | |
| SBRCA(3M, St. Paul MN) | 28.79 | 19.30 | 0.1719 | 0.1840 | sp | 40 | R | 0.9462 | 0.8367 |
| SBRCB(3M, St. Paul, MN) | 231.3 | 103.1 | −0.5317 | −0.3364 | sp | 40 | R | 0.9573 | 0.6894 |
| Resinomer Catalyst (Bisco) | 32.53 | 22.02 | −0.1596 | −0.0422 | sp | 40 | R | 0.9964 | 0.9676 |
| Resinomer Base (Bisco) | 38.81 | 27.44 | −0.07241 | −0.0129 | sp | 40 | R | 0.6155 | 0.4113 |
| Resiment Catalyst (Septodont) | 209.2 | 48.63 | −0.3853 | −0.0552 | sp | 40 | R | 0.9905 | 0.5744 |
| All-Bond C&B Catalyst (BISCO) | 140.1 | 73.64 | −0.1524 | 0.0036 | sp | 40 | R | 0.8451 | 0.1103 |
| Allbond C&B Base (BISCO) | 130.9 | 53.82 | −0.1487 | −0.0356 | sp | 40 | R | 0.5632 | 0.4282 |
| Resiment Base (Septodont) | 254.3 | 65.87 | −0.4247 | −0.0122 | sp | 40 | R | 0.9916 | 0.6193 |
| | | | | | | | R | | |

What is claimed is:

1. A method of adhering a prefabricated prosthetic device to an oral surface, the method comprising:
   preparing said oral surface;
   applying a dental resin cement material to the prefabricated prosthetic device, wherein said dental resin cement material comprises a mixture comprising:
   a) a filler;
   b) a polymerizable component, which may be monomers, oligomers, or polymers, containing a polymerizable group;
   c) a polymeric handling modifier, wherein the polymeric handling modifier has a weight average molecular weight between about 500 and about 100,000, and further wherein the polymeric handling modifier is selected from the group consisting of methacrylate modified polycaprolactonediols, polycaprolactonediols, methacrylate modified polyethylene glycols, polyethylene glycol methyl ethers, methacrylate modified polytetramethylene oxides, polytetramethylene oxides, N-polyvinyl pyrrolidones, polymeric ethoxylated Bisphenol A dimethacrylates, dicarboxy terminated polybutadienes, hydroxyl endcapped polybutadienes, copolymers of Bisphenol A and epichlorohydrin, and combinations thereof; and
   d) a polymerization initiator;
   wherein:
   the polymeric handling modifier and the polymerizable component are selected such that upon visual inspection by the unassisted eye of the polymeric handling modifier dispersed in the polymerizable component at 25° C. more than one phase cannot be discerned;
   components a), b), and c) are present in an amount effective to provide a material having a Viscosity vs Shear Rate Curve at a temperature of 25° C.±1° C. that fits a power law model curve fit of $F(x) = Ax^B$ wherein B is less than about −0.01, and said material correlating to said Curve at a correlation value greater than 0.85 for both increasing and decreasing shear rate over at least ten logarithmically spaced data points for both the increasing direction and the decreasing direction over a shear rate range, having a lowest value of 0.4–0.5 $s^{-1}$ and a highest value of 20–25 $s^{-1}$; and
   said dental resin cement material does not utilize water as its chemistry for curing;
   seating the device on the prepared oral surface;
   cleaning off the excess resin cement material from the margin between said oral surface and said device; and
   causing said dental resin cement material to polymerize and adhere the device to the oral surface.

2. The method of claim 1, wherein said correlation is greater than 0.9.

3. The method of claim 1, wherein B is less than about −0.1.

4. The method of claim 1, wherein B is between about −0.1 and about −1.1.

5. The method of claim 1, wherein A is greater than 10 and less than 3000.

6. The method of claim 1, wherein A is greater than 15 and less than 1000.

7. The method of claim 1, wherein A is greater than 20 and less than 500.

8. The method of claim 1, wherein for increasing shear rate, A is greater than or equal to about 40 and B is less than or equal to about −0.29, and for decreasing shear rate, A is greater than or equal to about 35 and B is less than or equal to about −0.26.

9. The method of claim 1, wherein the dental resin cement material comprises:
   a) a filler as 55–75% by weight;
   b) a polymerizable component present in an amount of no greater than 40% by weight; and
   c) a polymeric handling modifier as 0.1–25% by weight.

10. The method of claim 1, wherein said polymerizable component comprises a (meth)acrylate resin.

11. The method of claim 10, wherein said polymerizable component comprises a mixture of diglycidyl methacrylate of Bis-phenol A and triethylene glycol dimethacrylate.

12. The method of claim 1, wherein said polymerizable component comprises an epoxy.

13. The method of claim 1, wherein said polymerizable component comprises compounds selected from the group consisting of oxetanes, oxolanes, cyclic acetals, lactams, lactones, vinyl ethers, or spirocyclic compounds containing O atoms in the rings.

14. The method of claim 1, wherein said polymerizable component comprises polymers that are functionalized with acidic functionality.

15. The method of claim 1, wherein said polymerizable component and said polymeric handling modifier are the same compound.

16. The method of claim 15, wherein said polymerizable component and said polymeric handling modifier are both a polymeric ethoxylated Bisphenol A dimethacrylate having a weight average molecular weight between about 500 and 1000.

17. The method of claim 1, wherein said polymeric handling modifier is selected from polymers that are functionalized with acidic functionality.

18. The method of claim 1, wherein said polymeric handling modifier is selected from polymers that are functionalized with methacrylate functionality.

19. The method of claim 1, wherein said polymeric handling modifier is selected from polymers having a weight average molecular weight between about 500 and 50,000.

20. The method of claim 1, wherein said polymeric handling modifier is selected from polymers having a weight average molecular weight between about 700 and about 20,000.

21. The method of claim 1, wherein said dental resin cement material is substantially free of added water.

22. The method of claim 1, wherein said dental resin cement material further comprises acidic compounds.

23. The method of claim 1, wherein said dental resin cement material is free of acid reactive filler.

24. The method of claim 1, wherein the filler is a non-acid reactive filler, and the dental resin cement material further comprises an acidic functionality.

25. The method of claim 24, wherein said acidic functionality is provided as a separate acid compound.

26. The method of claim 24, wherein said acidic functionality is provided as a functional group on compounds of the polymerizable component.

27. The method of claim 1, wherein said prefabricated prosthetic device is selected from the group consisting of crowns, bridges, veneers, inlays, onlays, posts, and pins.

28. The method of claim 1 wherein said polymerizable component comprises esters of acrylic acid, esters of methacrylic acid, acrylamide, methacrylamide, substituted acrylamides, substituted methacrylamides, isopropenyl oxazolines, vinyl azalactones, vinyl pyrrolidone, styrene, divinylbenzene, urethane acrylates, urethane methacrylates, epoxy-containing materials, polyol acrylates, polyol methacrylates, oxetanes, oxolanes, cyclic acetals, lactams, lactones, vinyl ethers, spirocyclic compounds containing O atom in the rings, or combinations thereof.

29. The method of claim 1 wherein said polymerizable component, which may be monomers, oligomers, or polymers, contains a polymerizable group selected from the group of free radically polymerizable groups, cationically polymerizable groups, and mixtures thereof.

30. A method of adhering a direct restorative material to an oral surface, the method comprising:
preparing said oral surface;
applying a dental resin cement material to said prepared oral surface, wherein said dental resin cement material comprises a mixture comprising:
 a) a filler;
 b) a polymerizable component, which may be monomers, oligomers, or polymers, containing a polymerizable group;
 c) a polymeric handling modifier, wherein the polymeric handling modifier has a weight average molecular weight between about 500 and about 100,000, and further wherein the polymeric handling modifier is selected from the group consisting of methacrylate modified polycaprolactonediols, polycaprolactonediols, methacrylate modified polyethylene glycols, polyethylene glycol methyl ethers, methacrylate modified polytetramethylene oxides, polytetramethylene oxides, N-polyvinyl pyrrolidones, polymeric ethoxylated Bisphenol A dimethacrylates, dicarboxy terminated polybutadienes, hydroxyl endcapped polybutadienes, copolymers of Bisphenol A and epichlorohydrin, and combinations thereof; and
 d) a polymerization initiator;
 wherein:
  the polymeric handling modifier and the polymerizable component are selected such that upon visual inspection by the unassisted eye of the polymeric handling modifier dispersed in the polymerizable component at 25° C. more than one phase cannot be discerned;
  components a), b), and c) are present in an amount effective to provide a material having a Viscosity vs Shear Rate Curve at a temperature of 25° C. ±1° C. that fits a power law model curve fit of $F(x)=Ax^B$ wherein B is less than about −0.01, and said material correlating to said Curve at a correlation value greater than 0.85 for both increasing and decreasing shear rate over at least ten logarithmically spaced data points for both the increasing direction and the decreasing direction over a shear rate range, having a lowest value of 0.4–0.5 $s^{-1}$ and a highest value of 20–25 $s^{-1}$; and
  said dental resin cement material does not utilize water as its chemistry for curing;
placing the direct restorative material on said dental resin cement material applied to said prepared oral surface; and
causing said resin cement to polymerize and adhere the direct restorative material to the oral surface.

31. The method of claim 30, wherein said direct restorative material is a dental composite.

32. The method of claim 30, wherein said direct restorative material is an amalgam.

33. The method of claim 30 wherein said polymerizable component comprises esters of acrylic acid, esters of methacrylic acid, acrylamide, methacrylamide, substituted acrylamides, substituted methacrylamides, isopropenyl oxazolines, vinyl azalactones, vinyl pyrrolidone, styrene, divinylbenzene, urethane acrylates, urethane methacrylates, epoxy-containing materials, polyol acrylates, polyol methacrylates, oxetanes, oxolanes, cyclic acetals, lactams, lactones, vinyl ethers, spirocyclic compounds containing O atom in the rings, or combinations thereof.

34. The method of claim 30 wherein said polymerizable component, which may be monomers, oligomers, or polymers, contains a polymerizable group selected from the group of free radically polymerizable groups, cationically polymerizable groups, and mixtures thereof.

35. A method of adhering a direct restorative material or a prefabricated prosthetic device to a hard oral surface, the method comprising:
etching said oral surface;
applying an adhesive composition comprising polymerizable monomer and polymerization initiator to said etched oral surface;
causing said adhesive composition to polymerize on said surface;
applying a dental resin cement material to said adhesive treated surface, wherein said dental resin cement material comprises a mixture comprising:
 a) a filler;
 b) a polymerizable component, which may be monomers, oligomers, or polymers, containing a polymerizable group;
 c) a polymeric handling modifier, wherein the polymeric handling modifier has a weight average molecular weight between about 500 and about 100,000, and further wherein the polymeric handling modifier is selected from the group consisting of methacrylate modified polycaprolactonediols, polycaprolactonediols, methacrylate modified polyethylene glycols, polyethylene glycol methyl ethers, methacrylate modified polytetramethylene oxides, polytetramethylene oxides, N-polyvinyl pyrrolidones, polymeric ethoxylated Bisphenol A dimethacrylates, dicarboxy terminated polybutadienes, hydroxyl endcapped polybutadienes, copolymers of Bisphenol A and epichlorohydrin, and combinations thereof; and
 d) a polymerization initiator;
 wherein:
  the polymeric handling modifier and the polymerizable component are selected such that upon visual inspection by the unassisted eye of the polymeric handling modifier dispersed in the polymerizable component at 25° C. more than one phase cannot be discerned;
  components a), b), and c) are present in an amount effective to provide a material having a Viscosity vs Shear Rate Curve at a temperature of 25° C.±1° C. that fits a power law model curve fit of $F(x)=Ax^B$ wherein B is less than about −0.01, and said material correlating to said Curve at a correlation value greater than 0.85 for both increasing and decreasing shear rate over at least ten logarithmically spaced data points for both the increasing direction and the decreasing direction over a shear rate range, having a lowest value of 0.4–0.5 $s^{-1}$ and a highest value of 20–25 $s^{-1}$; and
  said dental resin cement material does not utilize water as its chemistry for curing;
applying the direct restorative material or the prefabricated prosthetic device to said dental resin cement material applied to said adhesive treated surface; and causing said dental resin cement material to polymerize and adhere the direct restorative material or prefabricated prosthetic device to the hard oral surface.

36. A method of adhering a prefabricated prosthetic device to a hard oral surface, the method comprising;

etching said oral surface;

applying an adhesive composition comprising polymerizable monomer and polymerization initiator to said etched oral surface;

causing said adhesive composition to polymerize on said surface;

applying a dental resin cement material to said prefabricated prosthetic device, wherein said dental resin cement material comprises a mixture comprising:
  a) a filler;
  b) a polymerizable component, which may be monomers, oligomers, or polymers, containing a polymerizable group;
  c) a polymeric handling modifier, wherein the polymeric handling modifier has a weight average molecular weight between about 500 and about 100,000, and further wherein the polymeric handling modifier is selected from the group consisting of methacrylate modified polycaprolactonediols, polycaprolactonediols, methacrylate modified polyethylene glycols, polyethylene glycol methyl ethers, methacrylate modified polytetramethylene oxides, polytetramethylene oxides, N-polyvinyl pyrrolidones, polymeric ethoxylated Bisphenol A dimethacrylates, dicarboxy terminated polybutadienes, hydroxyl endcapped polybutadienes, copolymers of Bisphenol A and epichlorohydrin, and combinations thereof; and
  d) a polymerization initiator;

wherein:
  the polymeric handling modifier and the polymerizable component are selected such that upon visual inspection by the unassisted eye of the polymeric handling modifier dispersed in the polymerizable component at 25° C. more than one phase cannot be discerned;
  components a), b), and c) are present in an amount effective to provide a material having a Viscosity vs Shear Rate Curve at a temperature of 25° C.±1° C. that fits a power law model curve fit of $F(x)= Ax^B$ wherein B is less than about −0.01, and said material correlating to said Curve at a correlation value greater than 0.85 for both increasing and decreasing shear rate over at least ten logarithmically spaced data points for both the increasing direction and the decreasing direction over a shear rate range, having a lowest value of 0.4–0.5 s$^{-1}$ and a highest value of 20–25 s$^{-1}$; and
  said dental resin cement material does not utilize water as its chemistry for curing;

seating the device on the adhesive treated surface;

cleaning off the excess dental resin cement material from the margin between said adhesive treated surface and said device; and causing said dental resin cement material to polymerize and adhere the device to the hard oral surface.

* * * * *

UNITED STATES PATENT AND TRADEMARK OFFICE
CERTIFICATE OF CORRECTION

PATENT NO. : 6,939,900 B2
DATED : September 6, 2005
INVENTOR(S) : Ario, Paula D.

It is certified that error appears in the above-identified patent and that said Letters Patent is hereby corrected as shown below:

Column 10,
Line 52, delete "diketoine" and insert -- diketone -- therefor.

Column 11,
Line 43, insert -- . -- after "thereof".

Column 15,
Line 43, delete "45%" and insert -- 4.5% --, therefor.

Column 16,
Line 59, delete "Examples," and insert -- Example 5, --, therefor.

Signed and Sealed this

Sixth Day of December, 2005

JON W. DUDAS
*Director of the United States Patent and Trademark Office*